(12) United States Patent
Habashi

(10) Patent No.: US 8,573,205 B2
(45) Date of Patent: *Nov. 5, 2013

(54) VENTILATION METHOD AND CONTROL OF A VENTILATOR BASED ON SAME

(75) Inventor: Nader Maher Habashi, Huntersville, NC (US)

(73) Assignee: Intensive Care On-Line Network, Inc., Baltimore, MD (US)

( * ) Notice: Subject to any disclaimer, the term of this patent is extended or adjusted under 35 U.S.C. 154(b) by 749 days.

This patent is subject to a terminal disclaimer.

(21) Appl. No.: 11/878,295

(22) Filed: Jul. 23, 2007

(65) Prior Publication Data

US 2008/0072901 A1 Mar. 27, 2008

Related U.S. Application Data

(63) Continuation of application No. 10/176,710, filed on Jun. 20, 2002, now Pat. No. 7,246,618.

(60) Provisional application No. 60/299,928, filed on Jun. 21, 2001.

(51) Int. Cl.
*A61M 16/00* (2006.01)

(52) U.S. Cl.
USPC .................................. 128/204.23; 128/204.22

(58) Field of Classification Search
USPC ............. 128/200.24, 203.12, 204.18, 204.21, 128/204.23
See application file for complete search history.

(56) References Cited

U.S. PATENT DOCUMENTS

| | | |
|---|---|---|
| 2,690,175 A | 9/1954 | George |
| 2,754,819 A | 7/1956 | Kirschbaum |
| 3,734,091 A | 5/1973 | Taplin |
| 3,741,208 A | 6/1973 | Jonsson et al. |
| 3,946,729 A | 3/1976 | Hanna |
| 4,036,221 A | 7/1977 | Hillsman et al. |
| 4,121,578 A | 10/1978 | Torzala |
| 4,206,754 A | 6/1980 | Cox et al. |
| 4,281,651 A | 8/1981 | Cox |
| 4,323,064 A | 4/1982 | Hoenig et al. |
| 4,326,513 A | 4/1982 | Schulz et al. |
| 4,773,411 A | 9/1988 | Downs |
| 5,103,814 A | 4/1992 | Maher |
| 5,107,830 A | 4/1992 | Younes |
| 5,186,167 A | 2/1993 | Kolobow |
| 5,255,675 A | 10/1993 | Kolobow |
| 5,390,666 A | 2/1995 | Kimm et al. |
| 5,596,984 A | 1/1997 | O'Mahoney et al. |
| 5,632,270 A | 5/1997 | O'Mahoney et al. |
| 5,884,622 A | 3/1999 | Younes |
| 5,909,731 A | 6/1999 | O'Mahoney et al. |

OTHER PUBLICATIONS

Drager; Evita 4 Intensive Care Ventilator operating Instructions Software 4.n; pp. 1-207.
"Airway Pressure release ventilation increases cardiac performance in patients with acute lung injury/adult respiratory distress syndrome" by Kaplan, et al. (cont.).
Critical Care Aug. 2001, vol. 5, No. 4, pp. 1-6.
Technical Data, Evita 4 Ventilator, 2005, 1 page.

*Primary Examiner* — Steven Douglas
(74) *Attorney, Agent, or Firm* — Corinne Marie Pouliquen

(57) ABSTRACT

The invention provides an improved ventilation method and method for controlling a ventilator apparatus in accordance with same. More specifically, the present invention relates to a method of controlling a ventilator apparatus comprising the steps of placing a ventilator in a mode capable of adjusting airway pressure (P) and time (T), monitoring expiratory gas flow, analyzing the expiratory gas flow over time (T) to establish an expiratory gas flow pattern, and setting and/or adjusting a low time (T2) based on the expiratory gas flow pattern. Alternatively, the present invention relates to a method of controlling a ventilator apparatus comprising the steps of placing a ventilator in a mode capable of adjusting airway pressure (P) and time (T), and setting a low airway pressure (P2) of substantially zero cmH$_2$O.

17 Claims, 8 Drawing Sheets

VENTILATION METHOD AND CONTROL OF A VENTILATOR BASED ON SAME

CROSS-REFERENCE TO RELATED APPLICATIONS

This application is a continuation of U.S. application Ser. No. 10/176,710 filed Jun. 20, 2002 now U.S. Pat. No. 7,246,618, which claims priority to U.S. Provisional Application No. 60/299,928 filed Jun. 21, 2001.

FIELD OF THE INVENTION

The invention relates to the field of ventilating human patients. More particularly, the present invention relates to an improved method for initiation, management and/or weaning of airway pressure release ventilation and for controlling a ventilator in accordance with same.

BACKGROUND OF THE INVENTION

Airway pressure release ventilation (APRV) is a mode of ventilation believed to offer advantages as a lung protective ventilator strategy. APRV is a form of continuous positive airway pressure (CPAP) with an intermittent release phase from a preset CPAP level. APRV allows maintenance of substantially constant airway pressure to optimize end inspiratory pressure and lung recruitment. The CPAP level optimizes lung recruitment to prevent or limit low volume lung injury. In addition, the CPAP level provides a preset pressure limit to prevent or limit over distension and high volume lung injury. The intermittent release from the CPAP level augments alveolar ventilation. Intermittent CPAP release accomplishes ventilation by lowering airway pressure. In contrast, conventional ventilation elevates airway pressure for tidal ventilation. Elevating airway pressure for ventilation increases lung volume towards total lung capacity (TLC), approaching or exceeding the upper inflection point. Limiting ventilation below the upper inflection of the P-V (airway pressure versus volume) curve is one of the goals of lung protective strategies. Subsequently, tidal volume reduction is necessary to limit the potential for over distension. Tidal volume reduction produces alveolar hypoventilation and elevated carbon dioxide levels. Reduced alveolar ventilation from tidal volume reduction has lead to a strategy to increase respiratory frequency to avoid the adverse effects of hypercapnia. However, increased respiratory frequency is associated with increase lung injury. In addition, increase in respiratory frequency decreases inspiratory time and the potential for recruitment. Furthermore, increasing respiratory frequency increases frequency dependency and decreases potential to perform ventilation on the expiratory limb of the P-V curve.

During APRV, ventilation occurs on the expiratory limb. The resultant expiratory tidal volume decreases lung volume, eliminating the need to elevate end inspiratory pressure above the upper inflection point. Therefore, tidal volume reduction is unnecessary. CPAP levels can be set with the goal of optimizing recruitment without increasing the potential for over distension. Consequently, end inspiratory pressure can be limited despite more complete recruitment and ventilation can be maintained.

Airway pressure release ventilation (APRV) was developed to provide ventilator support to patients with respiratory failure. Clinical use of APRV is associated with decreased airway pressures, decreased dead space ventilation and lower intra-pulmonary shunting as compared to conventional volume and pressure cycled ventilation. APRV limits excessive distension of lung units, thereby decreasing the potential for ventilator induced lung injury (VILI), a form of lung stress. In addition, APRV reduces minute ventilation requirements, allows spontaneous breathing efforts and improves cardiac output. APRV is also associated with reduction or elimination of sedative, inotropic and neuromuscular blocking agents.

APRV is a form of positive pressure ventilation that augments alveolar ventilation and lowers peak airway pressure. Published data on APRV has documented airway pressure reduction on the order of 30 to 75 percent over conventional volume and pressure cycled ventilation during experimental and clinical studies. Such reduction of airway pressure may reduce the risk of VILI. APRV improves ventilation to perfusion ratio ($V_A/Q$) matching and reduces shunt fraction compared to conventional ventilation. Studies performed utilizing multiple inert gas dilution and excretion technique (MIGET) have demonstrated less shunt fraction, and dead space ventilation. Such studies suggest that APRV is associated with more uniform distribution of inspired gas and less dead space ventilation than conventional positive pressure ventilation.

APRV has been associated with improved hemodynamics. In a 10-year review of APRV, Calzia reported no adverse hernodynamic effects. Several studies have documented improved cardiac output, blood pressure and oxygen delivery. Consideration of APRV as an alternative to pharmacological or fluid therapy in the hemodynamically-compromised, mechanically-ventilated patient has been recommended in several case reports.

APRV is a spontaneous mode of ventilation which allows unrestricted breathing effort at any time during the ventilator cycle. Spontaneous breathing in Acute Respiratory Distress Syndrome/Acute Lung Injury (ALI/ARDS) has been associated with improved ventilation and perfusion, decreased dead space ventilation and improved cardiac output and oxygen delivery. ALI/ARDS is a pathological condition characterized by marked increase in respiratory elastance and resistance. However, most patients with ALI/ARDS exhibit expiratory flow limitations. Expiratory flow limitations results in dynamic hyperinflation and intrinsic positive end expiratory pressure (PEEP) development. In addition, ARDS patients experience increased flow resistance from external ventilator valving and gas flow path circuitry including the endotracheal tube and the external application of PEEP.

Several mechanisms can induce expiratory flow limitations in ALI/ARDS. In ALI/ARDS both FRC and expiratory flow reserve is reduced. Pulmonary edema development and superimposed pressure result in increased airway closing volume and trapped volume. In addition, the reduced number of functional lung units (de-recruited lung units and enhanced airway closure) decrease expiratory flow reserve further. Low volume ventilation promotes small airway closure and gas trapping. In addition, elevated levels of PEEP increase expiratory flow resistance. In addition to downstream resistance, maximal expiratory flow depends on lung volume. The elastic recoil pressure stored in the proceeding lung inflation determines the rate of passive lung deflation.

APRV expiratory flow is enhanced by utilization of an open breathing system and use of low (0-5 $cmH_2O$) end expiratory pressure. Ventilation on the expiratory limb of the P-V curve allows lower PEEP levels to prevent airway closure. Lower PEEP levels result when PEEP is utilized to prevent de-recruitment rather than attempting partial recruitment. Increasing PEEP levels increases expiratory resistance, conversely lower PEEP reduce expiratory resistance, thereby accelerating expiratory flow rates. Sustained inflation results in increased lung recruitment (increased functional lung units and increased recoil pressure) and ventilation along the expiratory limb (reduced PEEP and expiratory flow resistance), improving expiratory flow reserve. In addition, release from a sustained high volume increases stored energy and recoil potential, further accelerating expiratory flow rates. Unlike low volume ventilation, release from a high lung volume increases airway caliber and reduces downstream resistance. Maintenance of end expiratory lung volume (EELV) to inflection point of the flow volume curve and the use of an open system allows reduction in circuitry flow resistance. EELV is maintained by limiting the release time and titrated to the inflection point of the flow volume curve. Reduced levels of end expiratory pressure are required when ventilation occurs on the expiratory limb of the P-V curve. In ALI/ARDS, increased capillary permeability results in lung edema. Exudation from the intravascular space accumulates, and superimposed pressure on dependent lung regions increases and compresses airspaces. Dependent airspace collapse and compressive atelectasis results in severe $V_A/Q$ mismatching and shunting. Regional transpulmonary pressure gradients which exist in the normal lung are exaggerated during the edematous phase of ALI/ARDS. Patients typically being in the supine position, forces directed dorsally and cephalad progressively increase pleural pressures in dependent lung regions. Ventilation decreases as pleural pressure surrounding the dependent regions lowers transalveolar pressure differentials. Full ventilatory support during controlled ventilation promotes formation of dependent atelectasis, increase $V_A/Q$ mismatching and intrapulmonary shunting. Increasing airway pressure can re-establish dependent trans-pulmonary pressure differential but at the risk of over distension of nondependent lung units. Alternatively, spontaneous breathing, as with APRV, can increase dependent transpulmonary pressure differentials without increasing airway pressure.

APRV allows unrestricted spontaneous breathing during any phase of the mechanical ventilator cycle. As noted, spontaneous breathing can lower pleural pressure, thereby increasing dependent transpulmonary pressure gradients without additional airway pressure. Increasing dependent transpulmonary pressure gradients improves recruitment and decreases $V_A/Q$ mismatching and shunt. As compared to pressure support ventilation (PSV) multiple inert gas dilution technique, APRV provides spontaneous breathing and improved $V_A/Q$ matching, intrapulmonary shunting and dead space. In addition, APRV with spontaneous breathing increased cardiac output. However, spontaneous breathing during pressure support ventilation was not associated with improved $V_A/Q$ matching in the dependent lung units. PSV required significant increases in pressure support levels (airway pressure) to match the same minute ventilation.

Conventional lung protective strategies are associated with increased use of sedative agents and neuromuscular blocking agents (NMBA). The increased use of sedative and NMBA may increase the time the patient must remain on mechanical ventilation ("vent days") and increase complications. NMBA are associated with prolonged paralysis and potential for nosocomial pneumonia. APRV is a form of CPAP and requires spontaneous breathing.

Decreased usage of sedation and neuromuscular blocking agents (NMBA) has been reported with APRV. In some institutions, APRV has nearly eliminated the use of NMBA, resulting in a significant reduction in drug costs. In addition to drug cost reduction, elimination of NMBA is thought to reduce the likelihood of associated complications such as prolonged paralysis and may facilitate weaning from mechanical ventilation.

Mechanical ventilation remains the mainstay management for acute respiratory failure. However, recent studies suggest that mechanical ventilation may produce, sustain or increase the risk of acute lung injury (ALI). Ventilator induced lung injury (VILI) is a form of lung stress failure associated with mechanical ventilation and acute lung injury. Animal data suggest that lung stress failure from VILI may result from high or low volume ventilation. High volume stress failure is a type of stretch injury, resulting from over distension of airspaces. In contrast, shear force stress from repetitive airway closure during the tidal cycle from mechanical ventilation results in low volume lung injury.

Initially, lung protective strategy focused on low tidal volume ventilation to limit excessive distension and VILI. Amato in 1995 and in 1998 utilized lung protective strategy based on the pressure-volume (P-V) curve of the respiratory system. Low tidal volumes (6 ml/kg) confined ventilation between the upper and lower inflection points of the P-V curve. End expiratory lung volume was maintained by setting PEEP levels to 2 $cmH_2O$ above the lower inflection point. Amato demonstrated improved survival and increased ventilator free days.

However, subsequent studies by Stewart and Bower were unable to demonstrate improved survival or ventilator free days utilizing low tidal volume ventilation strategy. Unlike Stewart and Bower, Amato utilized elevated end expiratory pressure in addition to tidal volume reduction. Such important differences between these studies limited conclusions as to the effectiveness of low tidal ventilation limiting ventilator associated lung injury (VALI).

Recent completion of the large controlled randomized ARDSNet trial documented improved survival and ventilator free days utilizing low tidal volume ventilation (6 ml/kg) vs. traditional tidal volume ventilation (12 ml/kg). Although the low tidal volume group (6 ml/kg) and traditional tidal volume group (12 ml/kg) groups utilized identical $PEEP/FiO_2$ scales, PEEP levels were significantly higher in the low tidal volume group. Higher PEEP levels were required in the low tidal volume group in order to meet oxygenation goals of the study. Despite improved survival in the low tidal volume group (6 ml/kg) over traditional tidal volume group (12 ml/kg), survival was higher in the Amato study. The ARDSNet trial also failed to demonstrate any difference in the incidence of barotrauma. The higher PEEP requirements and the potential for significant intrinsic PEEP from higher respiratory frequency in the lower tidal volume group, may have obscured potential contribution of elevated end expiratory pressure on survival. Further studies are contemplated to address the issue of elevated end expiratory pressure.

In the prior art, utilization of the quasi-static inspiratory pressure versus volume (P-V) curve has been advocated as the basis for controlling a ventilator to carry out mechanical ventilation. The shape of the inspiratory P-V curve is sigmoidal and is described as having three segments. The curve forms an upward concavity at low inflation pressure and a downward concavity at higher inflation pressures. Between the lower concavity and the upper concavity is the "linear" portion of the curve. The pressure point resulting in rapid transition to the linear portion of the curve has been termed the "lower inflection point". The lower inflection point is thought to represent recruitment of atelectatic alveolar units. The increasing slope of the P-V curve above lower inflection point reflects alveolar compliance. Above the inflection point, the majority of air spaces are opened or "recruited". Utilizing the lower inflection point of the inspiratory P-V curve plus 2 $cmH_2O$ has been proposed to optimize alveolar recruitment. Optimizing lung recruitment prevents tidal recruitment/de-recruitment and cyclic airway closure at end expiration. Ulti-

SUMMARY OF THE INVENTION

The invention provides an improved ventilation method and method for controlling a ventilator apparatus in accordance with same. The invention recognizes that ventilation utilizing elevated PEEP level prevents low volume lung injury. Setting PEEP levels above the inflection point of the expiratory flow curve is based on the notion that, at this level of PEEP, the majority of the airways are opened or recruited. In addition, this level of PEEP is thought to prevent airway closure or de-recruitment. Specifically, lung volume ($V_L$) increase at the level of inflection is thought to be related to increases in alveolar number ($V_N$) (recruitment). Thereafter the steeper inflection represents compliance of the recruited airspaces; the resulting lung volume increase is secondary to increase in alveolar volume ($V_A$)(non-recruitment volume change). The invention also recognizes that the P-V curve may not be a reliable indicator of recruitment. The P-V curve represents the entire respiratory system and may not adequately reflect the individual air spaces. Optimal PEEP levels at which cyclic airway closure is prevented are not yet precisely known, but are unlikely to be represented by a single point as contemplated in the prior art. The inventor believes it is more likely that recruitment occurs over a wide range of pressures. Furthermore, utilization of the inspiratory limb of the P-V curve may be of limited value in determining optimal PEEP levels. Events during recording of the P-V trace may affect the pressure-volume relationship. PEEP-induced recruitment may affect the slope of the P-V curve.

The invention further recognizes that recruitment continues above the inflection point and may continue at airway pressures beyond 30 cmH$_2$O and that the primary mechanism of lung volume change may be recruitment/de-recruitment (R/D) rather than isotropic and anisotropic alveolar volume change. Lung volume change to 80% of total lung capacity (TLC) may well be a result of alveolar number increase (R/D) rather than alveolar size. Furthermore, recruitment is an end inspiratory phenomenon and may be more closely related to plateau pressure rather than PEEP. Therefore, to prevent tidal recruitment/de-recruitment (R/D), cyclic shear stress and low volume lung injury, the invention contemplates that higher pressure may be required to achieve complete recruitment. It is recognized that if PEEP levels are set to end inspiratory pressure in order to completely recruit the lung, the superimposition of tidal ventilation could result in over-distension and high volume lung injury despite tidal volume reduction.

Accordingly, the invention recognizes that recruitment is an inflation phenomenon which continues beyond conventional PEEP levels. Recruitment requires enough pressure to overcome threshold-opening pressures and the superimposed pressure of the airspace. Plateau pressure or continuous positive airway pressure (CPAP) rather than PEEP level may be more appropriate determinants of full lung recruitment. PEEP conceptually prevents de-recruitment after a sustained inflation. Airway closure or de-recruitment is a deflation phenomenon. Therefore, in accordance with the invention, PEEP may be more suitable set to the inflection point of the deflation limb of the P-V curve rather than that of the inflation limb.

The deflation limb of the pressure volume curve reflects the differences between opening and closing pressures of airspaces (hysteresis). Higher airway pressures are necessary to open airspaces than are required to prevent airspaces closure. In pulmonary edema states, such as ALI/ARDS, the inflation limb of the P-V curve develops an increased pressure-volume relationship. Increased opening pressure results in greater pressure requirements for airspace opening. However, the deflation limb maintains a preserved pressure-volume relationship despite increasing pulmonary edema. Greater hysteresis results from a downward and right displacement of the inflation limb of the P-V curve. Therefore, ventilator control based on PEEP should be used to prevent airway closure rather than to cause airway opening. Using the deflation limb of the P-V curve is believed to have advantages for ventilation. Ventilation occurring on the more favorable pressure-volume relationship of the deflation curve reduces the level of PEEP required to prevent the same degree of airway closure (de-recruitment).

Rather than PEEP, plateau or CPAP levels should be utilized for bringing about airway opening (recruitment), allowing substantially complete recruitment. In addition to adequate threshold pressure, complete recruitment requires constant inflation in order to sustain recruitment. Furthermore, sustained recruitment facilitates ventilation on the deflation limb. Ventilation occurs on the deflation limb of the P-V curve only after a sustained recruitment maneuver. Sustained inflation pushes the P-V curve to the outer envelope on to the deflation limb. During the sustained inflation, the lung undergoes stress relaxation. Stress relaxation accounts for a pressure reduction on the order of 20% within the initial 4 seconds of inflation.

In accordance with the invention, APRV mode ventilation is established based on an initial set of ventilation parameters selected as described in further detail below. Once ventilation has been initiated, the parameter, T2, which defines the duration of the ventilator release phase, is monitored and adjusted according to at least one and preferably several alternative methods.

One method is to measure the expiratory gas flow rate during expiration and to adjust T2, if necessary, such that T2 is terminated when the rate of expiratory gas flow is at a value of about 25% to 50% of its absolute peak value during expiration. To achieve this, the ventilator is controlled to monitor the expiratory gas flow rate and terminate the release phase when the flow rate reaches a value within the aforementioned range.

Another method is to monitor expiratory flow and determine, based on the flow pattern, whether the flow is of a restrictive or obstructive nature, and adjust T2 accordingly. More particularly, T2 would be adjusted to a value of less than about 0.7 seconds in the event of restrictive flow and to a value greater than about 0.7 seconds in the event of obstructive flow. According to yet another method, the expiratory flow is monitored for the presence of an inflection point and T2 is adjusted as required to substantially eliminate or at least reduce the inflection point.

During management of ventilation in accordance with the invention blood oxygen and carbon dioxide levels are monitored. In the event of hypercarbia, the highest airway pressure achieved during inspiration (P1) and the duration of the positive pressure phase (T1) are both incrementally increased substantially contemporaneously once or more as needed until blood carbon dioxide declines to an acceptable level. Oxygenation is also regulated by adjusting P1 and T1 in a particular manner as will be described.

According to yet another aspect of the invention, weaning from ventilation is carried out by initiating a series of successive reductions in P1, each of which is accompanied by a substantially contemporaneous, increase in the duration of inspiration T1 such that over time, ventilation is transitioned from APRV to a substantially CPAP mode.

Applicant's ventilation method and method for controlling a ventilation apparatus based on same provides significant advantages over the prior art. These advantages include an increase in vent free days, lower ventilator-related drug costs, reduced ventilator associated complications, reduced likelihood of high volume lung injury, and reduced likelihood of low volume lung injury. These and other objects and advantages of the invention will become more apparent to a person of ordinary skill in the art in light of the following detailed description and appended drawings.

DETAILED DESCRIPTION

A patient in need of ventilation is intubated and connected to a mechanical ventilator which, except for being controlled in accordance with the present invention as described herein, can be of an otherwise known type such as the model known as Evita 4 distributed by Draeger Medical, Inc. of Telford, Pa. The ventilator includes pumps, valves and piping as well as all pressure, flow and gas content sensors required to carry out the invention. Operation of the ventilator is governed by a control unit which includes one or more processors. The control unit also includes both volatile and non-volatile electronic memory for the storage of operating programs and data. An operator interface coupled to the control unit typically includes a graphical user interface as well as a keyboard and/or pointing device to enable an operator to select the operating mode of the ventilator and/or to enter or edit patient data and operating parameters such as the pressures, times, flows, and/or volumes associated with one or more ventilation cycles. The interface also permits display, via a monitor, of measurements, trends or other data in alphanumeric and/or graphical format. The ventilator also includes a variety of sensors disposed in the ventilation gas circuit and/or elsewhere for measuring ventilation parameters including airway flow, airway pressure, and the makeup of inspiratory gasses, expiratory gasses and/or blood gasses including the partial pressures of oxygen and carbon dioxide in the bloodstream of the patient and the level of oxygen saturation of the blood. Based on pressure and flow measurements, the controller of the ventilator is also capable of calculating inspiratory and expiratory gas volumes. In addition, the control unit of the ventilator includes the capability to process data generated based on inputs from the sensors and determine variety parameters. For example, the ventilator can determine the ratio of inspiratory to expiratory effort based on flow measurements generated by flow meters associated with its inspiratory and expiratory valves. Such ratio is useful as an indicator of lung volume.

Figure 1:
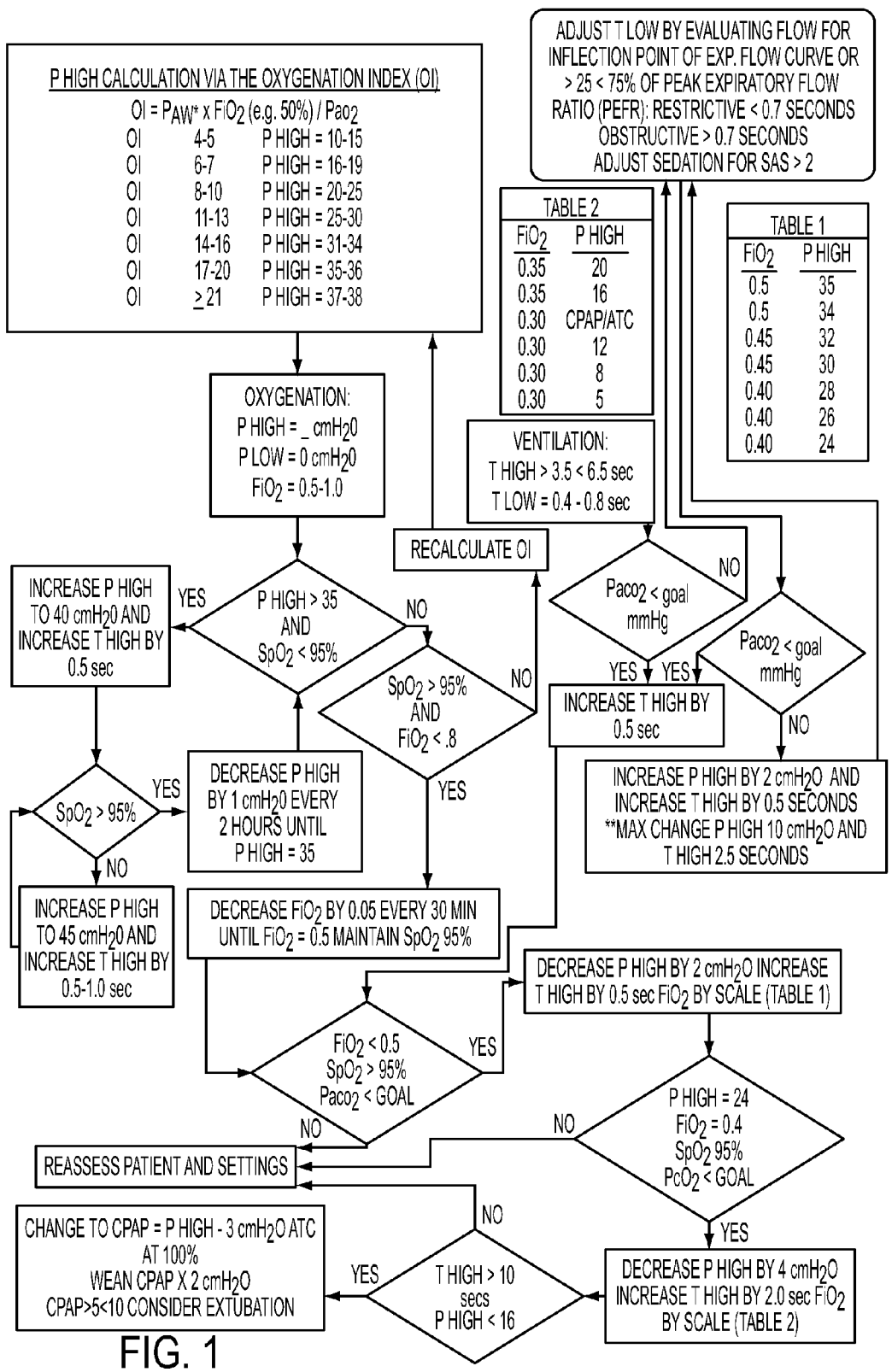
FIG. 1 is a flowchart illustrating a preferred embodiment of a ventilation method and control of a ventilator based on same according to the invention.

Referring to FIG. 1, the invention contemplates initiating ventilation of a patient in an APRV mode based on initial oxygenation and ventilation settings. The airway pressure during expiration (P2) is substantially zero throughout ventilation to allow for the rapid acceleration of expiratory gas flow rates. Typically, the fraction of oxygen in the inspired gas ($FiO_2$) is initially set at about 0.5 to 1.0 (i.e. about 50% to 100%). The highest airway pressure achieved during inspiration (P1) must be sufficiently high to overcome airspace closing forces and initiate recruitment of lung volume. P1 may suitably be initialized at a default value of about 35 $cmH_2O$. Alternatively, P1 may be established based either on the severity and type of lung injury or based on recruitment pressure requirements. The latter method is preferred in cases where the arterial oxygen concentration to fraction of inspired oxygen ratio (P/F) is less than or equal to about two hundred millimeters of mercury (200 mmHg). The P/F ratio is preferably monitored continuously. It is the ratio of the partial pressure of oxygen in the blood of the patient to the fraction of oxygen present in the inspired gas (i.e. $PaO_2/FiO_2$ but is commonly abbreviated as P/F).

Where the type and severity of lung injury are characterized by a P/F of greater than about 350 mmHg, an initial value of P1 within the range of about 20 $cmH_2O$ to 28 $cmH_2O$ is preferably established. On the other hand, if the P/F ratio is less than about 350 mmHg, P1 is preferably initialized within the range of about 28 $cmH_2O$ to 35 $cmH_2O$.

In situations where the P/F ratio is less than or equal to about 200 $cmH_2O$, such as may occur where the patient's initial injury is non-pulmonary and/or lung injury is of an indirect nature, the invention contemplates establishment of P1 at a value of between about 35 cm $H_2O$ and 40 $cmH_2O$ but preferably not appreciably above 40 $cmH_2O$. In cases where P1 is initially established at a default value of about 35 $cmH_2O$, P1 is reduced from such a value once P/F exceeds about 250 $cmH_2O$. Initiation of ventilation also requires the establishment of time (duration) settings for inspiration and expiration.

Initially, the duration of the positive pressure phase (T1) is established at a value within the range of about 5.0 to about 6.0 seconds unless the measured $PaCO_2$ is greater than about 60 mmHg. In that case, T1 is more preferably set to a lower initial value of within the range of about 4.0 to 5.0 seconds. The duration of the ventilator release phase (T2) may suitably be initialized at a value within the range of 0.5 to 0.8 seconds with about 0.7 seconds being a preferred default value.

Figure 2:
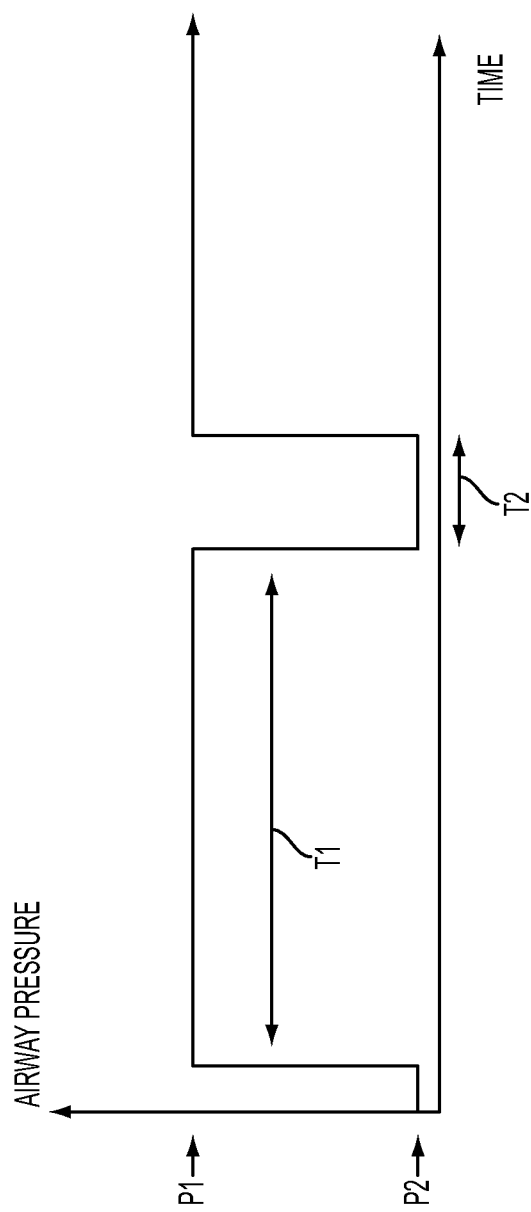
FIG. 2 is a schematic airway pressure versus time tracing for airway pressure release ventilation.

Once initial values of P1, P2, T1 and T2 have been established, ventilation continues in a repetitive APRV mode cycle generally as illustrated in FIG. 2. During management of ventilation in accordance with the invention, the initial values of one or more of these parameters are re-assessed and modified in accordance with measured parameters as will now be described with continued reference to FIG. 1.

Figure 5:
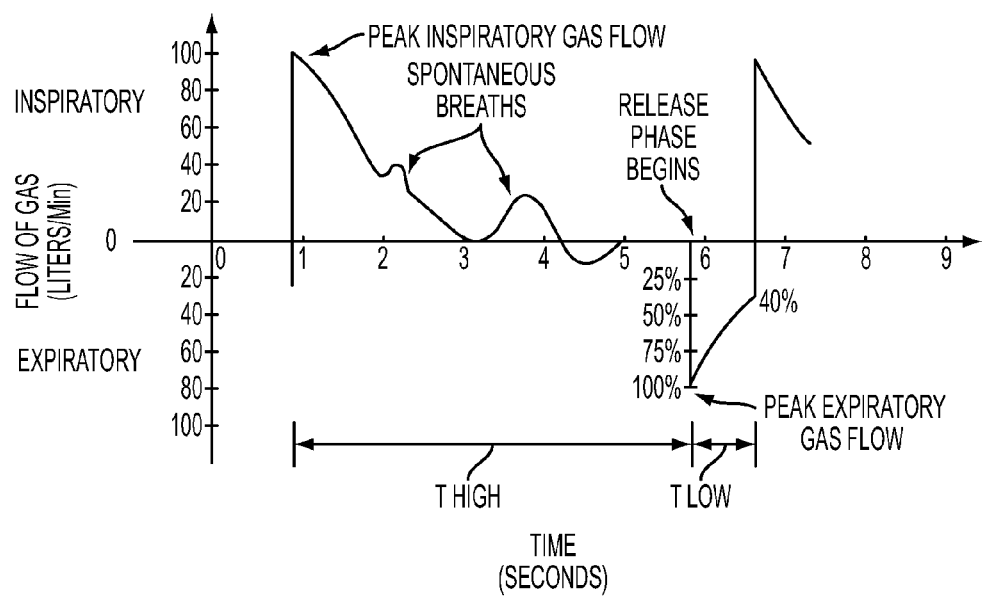
FIG. 5 is an inspiratory and expiratory gas flow versus time tracing for airway pressure release ventilation.

In management of ventilation in accordance with the invention, a principal goal is to maintain the level of carbon dioxide in the blood of the ventilated patient ($PaCO_2$) at a level of less than or equal to about 50 mmHg. Toward that end, arterial $PaCO_2$ is monitored continuously or measured as clinically indicated and the ventilator controlled to adjust ventilation as follows. Any time after ventilation has commenced, but preferably soon thereafter or promptly upon any indication of hypercarbia ($PaCO_2$ above about 50 mmHg), the setting of T2 is optionally but preferably checked and readjusted if necessary. According to the invention, optimal end expiratory lung volume is maintained by titration of the duration of the expiration or release phase by terminating T2 based on expiratory gas flow. To do so, the flow rate of the expiratory gas is measured by the ventilator and checked in relation to the time at which the controller of the ventilator initiates termination of the release phase. The expiratory exhaust valve should be actuated to terminate the release phase T2, at a time when the flow rate of the expiratory gas has decreased to about 25% to 50% of its absolute peak expiratory flow rate (PEFR). An example is illustrated in FIG. 5. In that example, T2 (sometimes referred to as Tlow) terminates by controlling the expiratory exhaust valve to terminate the release phase when the expiratory gas flow rate diminishes to 40% PEFR.

If monitoring of $PaCO_2$ indicates hypocarbia is present (i.e. $PaCO_2$ less than about 50 mmHg), T1 is increased by about 0.5 seconds while maintaining P1 substantially unchanged. Should the patient remain hypocarbic as indicated by subsequent measure of $PaCO_2$, weaning in the manner to be described may be initiated provided oxygenation is satisfactory and weaning is not otherwise contraindicated based on criteria to be described further below.

Figure 6:
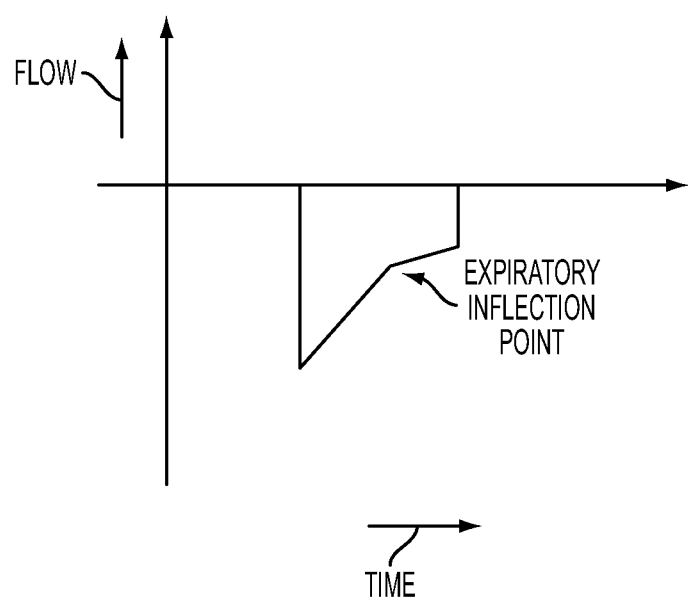
FIG. 6 is an expiratory gas flow versus time tracing.
Figure 7:
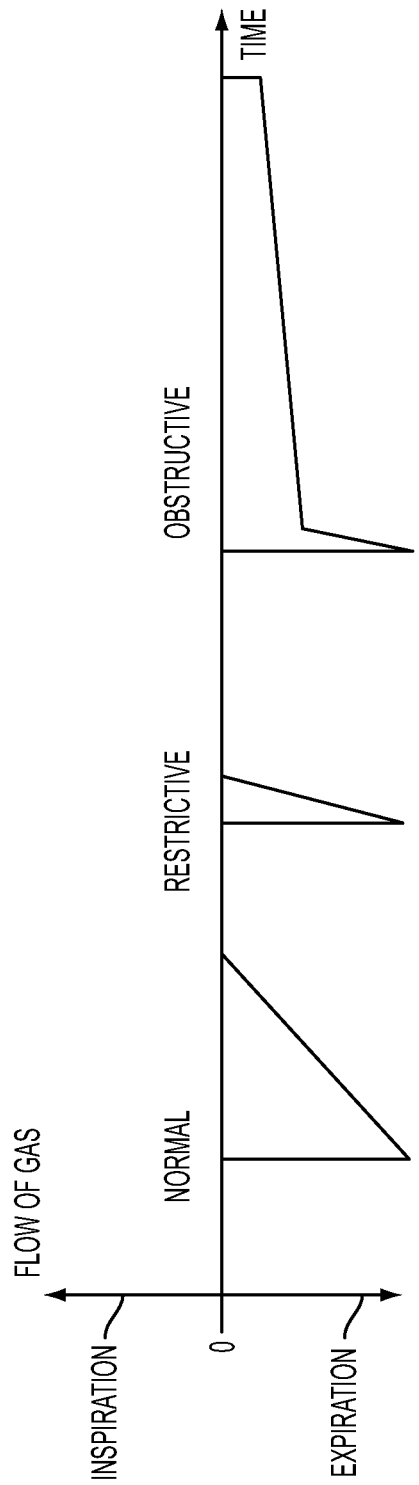
FIG. 7 is a set of expiratory gas flow versus time tracing illustrating determination of whether flow pattern is normal, restrictive or obstructive based on the shape of the tracing.

The hypercarbic patient though is not to be weaned. In the event of hypercarbia, the invention contemplates assessment of the expiratory flow pattern before making significant further adjustments to ventilation parameters. This assessment can readily be carried out by a software program stored within the control unit of the ventilator which carries out automated analysis of the expiration flow versus time tracing. As illustrated in FIG. 7, normal expiratory flow is characterized by flow which declines substantially monotonically from the onset of the release phase through its termination and does not fall off prematurely or abruptly. Restrictive flow in contrast declines rapidly from the onset of the release phase to zero or a relatively small value. Obstructive flow tends to be more extended in duration and is characterized by an inflection point beyond which the rate of flow falls off markedly from its initial rate. FIG. 6 illustrates another example of an obstructive flow pattern. Based on analysis of flow data provided by expiratory flow sensors, the control unit of the ventilator is programmed to determine whether flow is obstructive or restrictive based on the characteristics just described. If it is determined that obstructive or restrictive flow is present, the invention contemplates adjusting T2 before making any other significant adjustments to ventilation parameters. This can be done according to either of two alternative methods.

One method is to adjust T2 to a predetermined value according to whether flow is either obstructive or restrictive but allowing T2 to remain at its previous value if flow is normal. In the case of restrictive flow, T2 should be adjusted to less than about 0.7 seconds. On the other hand, obstructive flow calls for a T2 of greater duration, preferably greater than about 0.7 seconds with 1.0 to 1.2 being typical.

As FIG. 1 indicates, it is optional but advisable to promptly assess the sedation level of the hypercarbic patient. Sedation of the patient can be evaluated by any suitable technique such as the conventional clinical technique of determining an SAS score for the patient. If the patient appears over-sedated based on the SAS score (SAS score greater than about 2) or otherwise, reduction of sedation should be considered and initiated if appropriate. Thereafter, as FIG. 1 indicates, T1 should be increased by about 0.5 seconds and P1 increased concomitantly by about 2 $cmH_2O$. After allowing sufficient time for these adjustments to take effect on the patient, $PaCO_2$ should be re-evaluated. If the patient remains hypercarbic, T1 should be increased again by about 0.5 seconds and P1 again increased concomitantly by about 2 $cmH_2O$. $PaCO_2$ should then be reassessed and concomitant increases of about 0.5 seconds in T1 and about 2 $cmH_2O$ in P1 repeated as indicated in FIG. 1 until the patient is no longer hypercarbic. However, the total duration of T1 should not be increased beyond a maximum of about fifteen (15) seconds.

Management of oxygenation in accordance with the invention is carried out with the goal of maintaining the level of oxygen in the arterial blood of the ventilated patient ($PaO_2$) at a value of at least about 80 mmHg and a maintaining saturation level ($SaO_2$) of at least about 95%. Preferably fluctuation of $PaO_2$ are held within a target range of about 55 mmHg and 80 mmHg. (Expressed in terms of $SpO_2$, the target range would be between about 0.88 and 0.95 though where $PaO_2$ and $SpaO_2$ data are both available, $PaO_2$ would take precedence.) Responsive to a determination that oxygenation and saturation both meet the goals just specified, the ventilator would be controlled to progressively decrease the fraction of oxygen in the inspired gas ($FiO_2$) by about 0.05 about every thirty minutes to one hour with the objective of maintaining a blood oxygen saturation level ($SaO_2$) of about 95% at a P1 of about 35 and an $FiO_2$ of about 0.05. Upon meeting the latter objective, weaning in the manner to be described may be initiated provided the ventilation goal described earlier (i.e. a $PaCO_2$ of less than about 50 mmHg) is met and weaning is not otherwise contraindicated.

However, if the goals of oxygenation of $PaO_2$ of at least about 80 mmHg and arterial blood oxygen saturation ($SaO_2$) of at least about 95% cannot both be maintained at the then-current $FiO_2$, $FiO_2$ is not decreased. Instead, P1 is increased to about 40 $cmH_2O$ and T1 increased substantially contemporaneously by about 0.5 seconds. If such action does not result in raising oxygenation and saturation to at least the goals of about $PaO_2$ of about 80 mmHg and $SaO_2$ of about 95%, P1 is increased to a maximum of about 45 $cmH_2O$ and T1 is progressively further increased by about 0.5 seconds to 1.0 seconds. Oxygenation and saturation are then re-evaluated and, if they remain below goal, $FiO_2$, if initially less than 1.0, may optionally be increased to about 1.0. Oxygen and saturation continue to be re-evaluated and, T1 successively raised in increments of about 0.5 to 1.0 seconds until the stated oxygen and saturation goals are met.

Once those oxygenation and saturation goals are met, ventilation is controlled to maintain those goals while progressively decreasing $FiO_2$ and P1 toward the levels at which initiation of weaning can be considered. More particularly, P1 is decreased by about 1 $cmH_2O$ per hour while $FiO_2$ is decreased by about 0.05 about every thirty (30) minutes while maintaining an oxygen saturation of at least about 95%.

Figure 3:
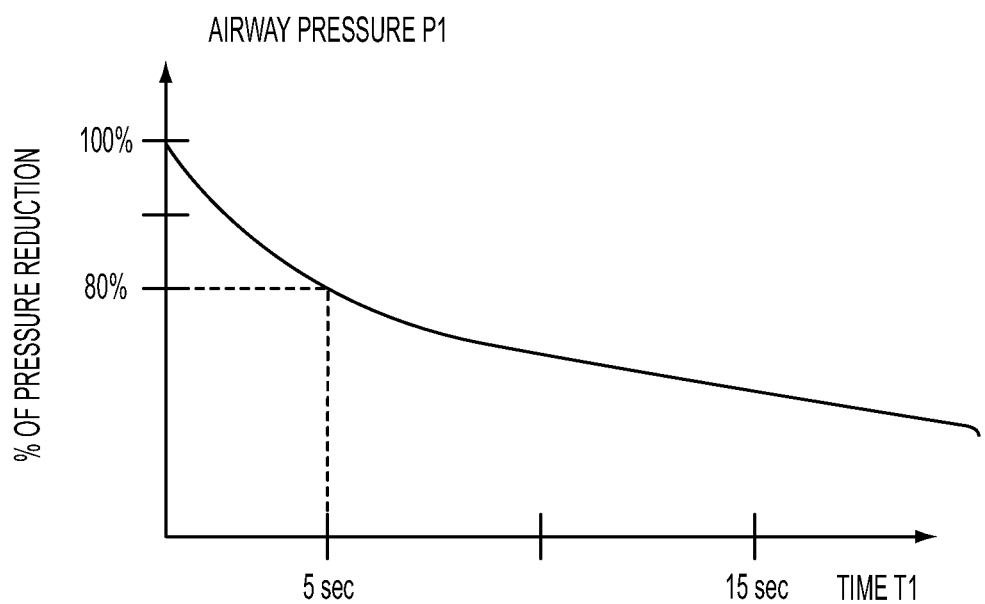
FIG. 3 is a airway pressure versus time tracing during the inspiratory (P1) phase of ventilation.
Figure 4:
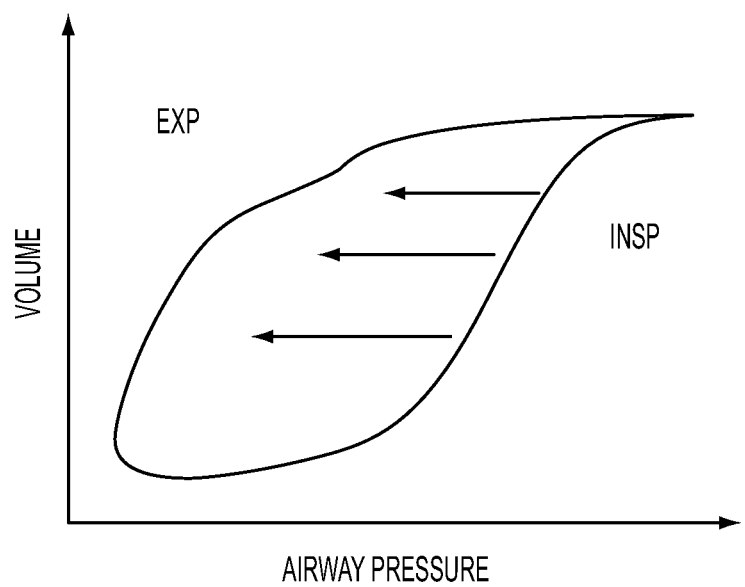
FIG. 4 is an airway volume versus pressure curve illustrating a shift from the inspiratory limb to the expiratory limb thereof.
Figure 8:
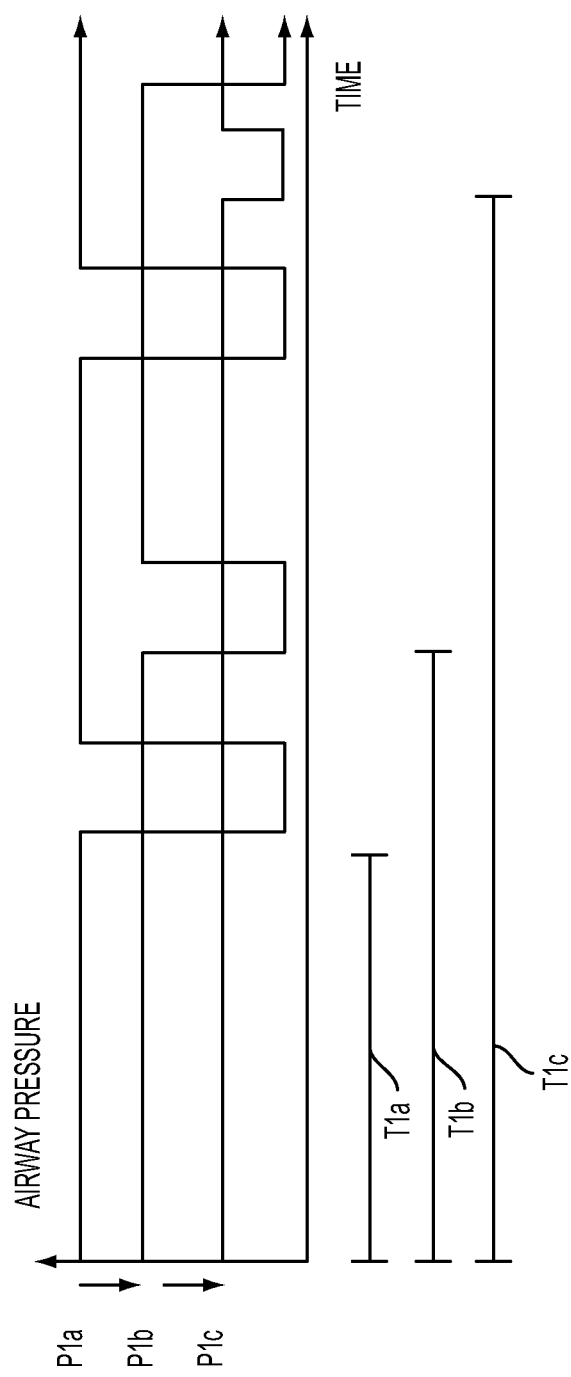
FIG. 8 is a set of airway pressure versus time tracings illustrating ventilation weaning by successive reductions in pressure P1 and substantially contemporaneous increases in time T1.

Weaning according to the invention, unless otherwise contraindicated, may commence after the oxygenation and ventilation goals described above have been met. That is, when $PaCO_2$ remains below about 50 mmHg and $SaO_2$ remains at least about 95% at a P1 of about 35 $cmH_2O$ and $FiO_2$, if previously higher, has been weaned to a level of not greater than about 0.5. During weaning in accordance with the invention, T1 is controlled to sustain recruitment while P1 is reduced to gradually reduce airway pressure. As FIG. 8 illustrates, this is achieved by carrying out a series of successive incremental reductions in P1 while substantially contemporaneously[1] carrying out a series of successive incremental increases in T1 so as to induce gradual pulmonary stress relaxation as FIG. 3 illustrates. As a result, the inspiratory pressure versus volume curve shifts progressively from its inspiratory limb to its expiratory limb as illustrated in FIG. 4.

In a preferred embodiment as illustrated in FIG. 1, weaning is carried out in two stages, the first of which is more gradual than the second. During the first stage, P1 is reduced by about 2 cmH$_2$O about every hour. Substantially contemporaneously with each reduction in P1, T1 is increased by about 0.5 to 1.0 seconds up to, but not in excess of a T1 of about 15 seconds in total duration. As P1 is being reduced in the manner just described, the fraction of oxygen in the inspired gas (FiO$_2$) is also gradually reduced in accordance with P1. During the first stage of weaning, this gradual weaning of FiO$_2$ is carried out substantially in accordance with Table 1 of FIG. 1. When P1 has been reduced to about 24 cmH$_2$O and FiO$_2$ weaned to about 0.4 with the patient sustaining a blood oxygen saturation (SaO$_2$) of at least about 95% weaning may proceed to the more aggressive second stage.

[1] The term "substantially contemporaneously" should not be construed to be limited to necessarily require that changes occur precisely at the same moment. Rather, the term is to be construed broadly to encompass not merely events that occur at the same time, but also any which are close enough in time to achieve the advantages or effects described.

During the second stage, as FIG. 1 indicates, successive reductions in P1 and substantially contemporaneous increases in T1 continue about once every hour. However, during the second stage, the reductions in P1 take place in increments of about 4 cmH$_2$O and the increases in T1 are each about 2.0 seconds. As reductions in P1 continue, further weaning of FiO$_2$ is implemented substantially in accordance with Table 2 of FIG. 1. Once FiO$_2$ is weaned to about 0.3, airway pressures are reduced such that the ventilation mode by then has been transitioned from APRV to a substantially Continuous Positive Airway Pressure/Automatic Tube Compensation Mode (CPAP/ATC).

Once the patient is tolerating CPAP at about 5 cmH$_2$O with FiO$_2$ of not greater than about 0.5, the patient's ability to maintain unassisted breathing is assessed, preferably for at least about 2 hours or more.

a.) SpO$_2$ of at least about 0.90 and/or PaO$_2$ of at least about 60 mmHg;
 b.) tidal volume of not less than about 4 ml/kg of ideal bodyweight;
 c.) respiration rate not significantly above about 35 breaths per minute, and
 d.) lack of respiratory distress, with such distress being indicated by the presence of any two or more of the following:
  i) Heart rate greater than 120% of the 0600-hour rate (though less than about 5 minutes above such rate may be considered acceptable)
  ii) marked use of accessory muscles to assist breathing;
  iii) thoroco-abdominal paradox;
  iv) diaphoresis and/or
  v) marked subjected dyspnea.

If there is an indication of respiratory distress, CPAP at an airway pressure of about 10 cmH$_2$O should be resumed and monitoring and reassessment carried out as needed. However, if criteria a) through d) above are all satisfied, the patient may be transitioned to substantially unassisted breathing such as by extubation with face mask, nasal prong oxygen or room air, T-tube breathing, tracheotomy mask breathing or use of high flow CPAP at about 5 cmH$_2$O.

During all phases of ventilation including initiation, management and weaning, the patient should be reassessed at least about every two hours and more frequently if indicated. Blood gas measurements (PaO$_2$, SaO$_2$ and PaCO$_2$) that govern control of ventilation according to the invention should be monitored not less frequently than every two hours though substantially continuous monitoring of all parameters would be considered ideal.

Just prior to and during weaning at least one special assessment should be conducted daily, preferably between 0600 and 1000 hours. If not possible to do so, a delay of not more than about four hours could be tolerated. Weaning should not be initiated or continued further unless:

a) at least about 12 hours have passed since initial ventilation settings were established or first changed,
 b) the patient is not receiving neuromuscular blocking agents and is without neuromuscular blockade, and
 c) Systolic arterial pressure is at least about 90 mmHg without vasopressors (other than "renal" dose dopamine).

If these criteria are all met, a trial should be conducted by ventilating the patent in CPAP mode at about 5 cmH$_2$O and an FiO$_2$ of about 0.5 for about five (5) minutes. If the respiration rate of the patient does not exceed about 35 breaths per minute (bpm) during the five (5) minute period weaning as described above may proceed. However, if during the five (5) minute period the respiration rate exceeds about 35 bpm it should be determined whether such tachypnea is associated with anxiety. If so, administer appropriate treatment for the anxiety and repeat the trial within about four (4) hours. If tachypnea does not appear to be associated with anxiety, resume management of ventilation at the parameter settings in effect prior to the trial and resume management of ventilation as described above. Re-assess at least daily until weaning as described above can be initiated.

What I claim is:

1. A method of controlling a ventilator apparatus comprising the steps of:
 a) placing a ventilator in a mode capable of adjusting airway pressure (P) and time (T);
 b) monitoring expiratory gas flow;
 c) analyzing the expiratory gas flow over time (T) to establish an expiratory gas flow pattern, and
 d) setting a low time (T2) based on the expiratory gas flow pattern.

2. The method of claim 1, further comprising the steps of monitoring inspiratory gas flow and determining expiratory and inspiratory gas volume.

3. The method of claim 1, further comprising the steps of setting a low airway pressure (P2) of substantially zero cmH$_2$O.

4. The method of claim 3, further comprising the steps of:
 a) monitoring inspiratory gas flow,
 b) determining the relationship between the expiratory and inspiratory gas flow, and
 c) setting a high airway pressure (P1).

5. The method of claim 4, wherein the step of determining the relationship comprises determining the ratio of the expiratory gas flow and the inspiratory gas flow.

6. The method of claim 4, further comprising the steps of analyzing the expiratory and inspiratory gas flow over time (T) to establish an expiratory and inspiratory gas flow pattern and analyzing the expiratory and inspiratory gas flow pattern.

7. The method of claim 3, wherein the mode comprises a preset continuous positive airway pressure (CPAP) level mode with an intermittent pressure release.

8. The method of claim 7, further comprising the step of substantially simultaneously adjusting a high airway pressure (P1) and a high time (T1).

9. The method of claim 3, further comprising the steps of:
 a) monitoring blood carbon dioxide levels for hypercarbia,
 b) increasing a high time (T1) and maintaining a high pressure (P1) substantially unchanged.

10. The method of claim 3, further comprising the steps of:
   a) monitoring blood oxygen levels, and
   b) increasing a high airway pressure (P1) and a high time (T1) substantially contemporaneously to raise oxygenation levels.

11. The method of claim 10, wherein P1 is increased to a maximum of about 45 $cmH_2O$.

12. The method of claim 11, further comprising the steps of subsequently decreasing P1 at a rate of about 1 $cmH_2O$ per hour and maintaining oxygen levels.

13. The method of claim 3, further comprising the step of controlling the ventilator with a control unit.

14. The method of claim 13, wherein the control unit is programmed to analyze the expiratory gas flow over time.

15. A method of controlling a ventilator apparatus comprising the steps of:
   a) placing a ventilator in a mode capable of adjusting airway pressure (P) and time (T),
   b) setting a low airway pressure (P2) of substantially zero $cmH_2O$,
   c) monitoring blood $CO_2$ levels, and
   d) increasing the high time (T1) interval and decreasing the high airway pressure (P1).

16. The method claim 15, wherein the monitoring comprises determining whether the blood $CO_2$ levels are normal or below normal.

17. The method of claim 1, further comprising the steps of setting low airway pressure (P2) of no more than zero $cmH_2O$.

* * * * *

UNITED STATES PATENT AND TRADEMARK OFFICE
CERTIFICATE OF CORRECTION

PATENT NO. : 8,573,205 B2
APPLICATION NO. : 11/878295
DATED : November 5, 2013
INVENTOR(S) : Nader M. Habashi Page 1 of 1

It is certified that error appears in the above-identified patent and that said Letters Patent is hereby corrected as shown below:

In the Specification

Column 2, line 24, change "hernodynamic" to --hemodynamic--,
    line 27, change "hemodynamically-compromised" to --hemodynamically compromised--, and
    line 28, change "mechanically-ventilated" to --mechanically ventilated--.
Column 3, line 9, replace "volume" with --time--,
    line 12, replace "volume" with --time--, and
    line 59, before "requires" add --preferably--.
Column 4, line 22, change "Bower" to --Brower--, and
    line 25, change "Bower" to --Brower--.
Column 7, line 67, after "determine" insert --a--, and
    line 67, after "variety" insert --of--.
Column 8, line 34, change "$cmH_2O$" to --mmHg--, and
    line 41, change "$cmH_2O$" to --mmHg--.
Column 10, line 12, change "fluctuation" to --fluctuations--,
    line 16, change "$SpaO_2$" to --$SpO_2$--,
    line 24, change "0.05" to --0.5--.
Column 11, line 11, change "ofFIG." to --of FIG.--,
    line 49, change "thoroco-abdominal" to --thoraco-abdominal--, and
    line 51, change "subjective" to --subjected--.
Column 12, line 15, change "patent" to --patient--.

Signed and Sealed this
Twenty-first Day of April, 2015

Michelle K. Lee
*Director of the United States Patent and Trademark Office*